United States Patent
Yang et al.

(10) Patent No.: US 10,617,559 B2
(45) Date of Patent: Apr. 14, 2020

(54) HIGH-PRECISION DRUG DELIVERY BY DUAL-DOMAIN OCULAR DEVICE

(71) Applicant: LYNTHERA CORPORATION, Lancaster, PA (US)

(72) Inventors: Arthur Jing-Min Yang, York, PA (US); Roman C. Domszy, Lancaster, PA (US); Jeffry Chung-Hwang Yang, York, PA (US)

(73) Assignee: Lynthera Corporation, Lancaster, PA (US)

( * ) Notice: Subject to any disclaimer, the term of this patent is extended or adjusted under 35 U.S.C. 154(b) by 0 days.

(21) Appl. No.: 16/370,407

(22) Filed: Mar. 29, 2019

(65) Prior Publication Data

US 2019/0224045 A1    Jul. 25, 2019

Related U.S. Application Data (63) Continuation of application No. PCT/US2017/054505, filed on Sep. 29, 2017.

(60) Provisional application No. 62/402,509, filed on Sep. 30, 2016.

(51) Int. Cl.
| | |
|---|---|
| *A61L 27/54* | (2006.01) |
| *A61F 9/00* | (2006.01) |
| *G02C 7/04* | (2006.01) |
| *A61K 9/00* | (2006.01) |
| *A61M 31/00* | (2006.01) |

(52) U.S. Cl.
CPC .......... *A61F 9/0017* (2013.01); *A61K 9/0051* (2013.01); *A61L 27/54* (2013.01); *G02C 7/04* (2013.01); *A61L 2300/624* (2013.01); *A61L 2300/626* (2013.01); *A61L 2430/16* (2013.01); *A61M 31/002* (2013.01)

(58) Field of Classification Search
CPC .............. A61K 27/54; A61K 2300/624; A61K 2300/626; A61K 2430/16; A61M 31/002; A61F 9/0017; G02C 7/04
See application file for complete search history.

(56) References Cited

U.S. PATENT DOCUMENTS

| | | | |
|---|---|---|---|
| 5,034,166 A | 7/1991 | Rawlings et al. | |
| 5,928,662 A | 7/1999 | Phillips | |
| 2003/0064088 A1 | 4/2003 | Carvalho et al. | |
| 2005/0013863 A1* | 1/2005 | Lim ..................... | A61K 9/0065 424/472 |
| 2011/0244010 A1* | 10/2011 | Doshi .................. | A61K 9/0051 424/402 |
| 2012/0109054 A1 | 5/2012 | Thompson et al. | |
| 2013/0296833 A1 | 11/2013 | Blaskovich et al. | |

OTHER PUBLICATIONS

Paradiso et al., "ControlledRelease of Antibiotics From Vitamin E-Loaded Silicone-Hydrogel Contact Lenses", 2016, vol. 105, pp. 1164-1172. (Year: 2016).*
International Search Report dated Dec. 14, 2017 issued in PCT/US17/54505.

* cited by examiner

*Primary Examiner* — Ali Soroush
(74) *Attorney, Agent, or Firm* — Perkins Coie LLP; Viola T. Kung (57) ABSTRACT

The present invention relates to a nanocomposite ocular device that can release drugs within a close distance to the ocular surface and provide controlled and sustained release of the drug at a constant rate. The device can achieve both optical and medical functions. The device comprises a drug, one or more reservoir domains, and a barrier layer configured to block the drug diffusion paths from the reservoir domain to the ocular surface in the eye of the subject, wherein the drug partitions between the reservoir domain and the barrier layer, and the equilibrium drug solubility in the reservoir domain is at least five folds higher than that in the barrier layer.

17 Claims, 5 Drawing Sheets

FIG. 1A        FIG. 1B

Solubility Saturation for Rate Control

FIG. 2

$$J_{barrier} = D_{barrier} \cdot \frac{C_{in} - C_{out}}{d}$$

$$= J_{adsorption} + J_{turnover}$$

Adjusting thickness and diffusion coefficient of the barrier layer so that $D_{barrier} \cdot \frac{C_0^{satu.} - kC_{eff}}{d}$ equals the sum of adsorption and turnover fluxes.

HIGH-PRECISION DRUG DELIVERY BY DUAL-DOMAIN OCULAR DEVICE

This application is a continuation of PCT/US2017/054505, filed Sep. 29, 2017; which claims the benefit of U.S. Provisional Application No. 62/402,509, filed Sep. 30, 2016. The contents of the above-identified applications are incorporated herein by reference in their entirety.

FIELD OF THE INVENTION

The present invention relates to a drug-eluting nanoengineered ocular device comprising a drug, one or more reservoir domains, and a barrier layer configured to block the drug diffusion paths from the reservoir domain to the ocular surface in the eye of the subject, wherein the drug partitions between the reservoir domain and the barrier layer, and the equilibrium drug solubility in the reservoir domain is at least five folds higher than that in the barrier layer.

BACKGROUND OF THE INVENTION

The past decade has seen a great increase in patients wearing prescription contact lenses and color contact lenses in order to correct visual sensation and change appearance of eyes. The advancement in silicone-hydrogel composite technology has improved both the water affinity and oxygen permeability of a contact lens and transformed it into a breathable and hydrophilic soft tissue. Integrating this hydrophobic-hydrophilic nanocomposite technology with other advancements in materials and medical nanotechnology, we can develop a new generation of nanoengineered ocular device that has the same optical performance and ease of use as a contact lens, but with many more medical applications beyond simple vision correction. Because such an ocular device is in constant contact with tear fluids at the most observable location of the eye, and is easily applied and removed, it can function as the most convenient implantable medical device for diagnostics, drug delivery, wound healing, and in particular, as a groundbreaking tool in ocular disease therapy.

Delivering a drug to the eye at high therapeutic efficacy is challenging due to the eye's complexity, including high sensitivity to foreign stimuli, protective mechanisms (e.g., blinking, tears), and several overlaying diffusion barricades (Short B, Soc Toxicol Pathol 2008; 36: 49-62). The two main alternatives to implants have serious limitations and drawbacks as follows.

1. Topical application of eye drops results in a sudden, burst dosage that is difficult to control, and further hindered by tear drainage along with corneal and scleral barriers to the point that only about 5% of functional ingredients deliver to the target, and 2. Intravitreal injection, while direct and efficacious, also gives a burst dosage that raises intraocular pressure, and requires repeated administration that bears risks to the patient's eye including hemorrhage, cataract, retinal wounds and even retinal detachment.

There is a need for an ocular device that can effectively deliver a drug to the eye and release the drug at a dosage rate that is precisely controllable and sustainable.

DETAILED DESCRIPTION OF THE INVENTION

Definitions

A "drug" as used herein, refers to a molecule having an activity to cause a physiological change in a subject, such as a pharmaceutical drug or a nutrient. For example, a drug can be a prescription drug as regulated by FDA, including, but not limited to, antibiotics (fluoroquinolone), glaucoma drugs (bimatoprost), dry eye drugs (cyclosporine), macular degeneration drugs (bevacizumab), or steroids (difluprednate); or an over-the-counter drug as regulated by FDA, including, but not limited to, artificial tears (carboxymethylcellulose) or contact lens solution; or a macronutrient such as a carbohydrate, protein, or fat (omega-3 fatty acids).

The "solubility parameter" of a substrate is an approximate measure of molecular interaction between identical molecules. When two different types of molecules are mixed in one solution, the square of the difference of the two solubility parameters reflects the energy penalty of mixing. Thus, the greater the difference in solubility parameters, the lesser the solubility, which is the basis of the principle "like dissolves like."

The "hydrophobic/hydrophilic" ratio is a measure of a material's hydrophobicity based on its solubility and partition between hydrophobic octanol and hydrophilic water. It is normally referred to a material constant log P of octanol/water, where P is a partition coefficient of a soluble component between octanol and water (Sangster J, J Phys Chem Ref Data 1989; 18: No. 3). A positive log P value means hydrophobic and a negative value means hydrophilic. A differential of log P less than 0.5 between two components means they are of a similar (alike) nature, while a differential of log P greater than 1 means the two components are of opposite (dislike) nature. Thus. the difference in log P has the same implication as the difference in solubility parameters. However, both measures are just qualitative, not quantitative, descriptions of the solubility behavior of the mixing components.

The inventors of the present invention have discovered a nanocomposite ocular device that can release one or more drugs within a close distance (about 10µ) to the cornea and at a dosage rate that is precisely controllable and sustainable. This device has similar optical quality (i.e., transparent) to a vision-corrective contact lens. The device can be non-surgically (i.e. by hand, or with use of a tool) overlaid either in contact with the tear film above the cornea or sclera, or directly onto the cornea or sclera. The device can achieve both optical and medical functions. An optically and medically combined function means the portion of the device covering the cornea must be highly transparent (transmission rate over 90%), with or without vision corrective power, while the device achieves one or more desired medical function (i.e., drug delivery, tissue engineering, sensing, diagnosing, orthokeratology, environmental responses, etc.).

The present invention is directed to a transparent ocular device for delivering one or more drug to the eye of a subject. The device comprises: (i) at least a drug, (ii) one or more reservoir domains, and (iii) a barrier domain of layer configuration (or a barrier layer) to block the drug diffusion paths from the reservoir domain to the ocular surface in the eye of the subject; wherein the drug partitions between the reservoir domain and the barrier layer, and the equilibrium drug solubility in the reservoir domain is at least five folds higher than that in the barrier layer, such that when the device is placed directly onto the ocular surface or in contact with the tear film above the ocular surface in the eye, the device provides controlled and sustained release of the drug at a constant rate. In one embodiment, the device is a drug-delivery optical lens optionally having refractive power to correct myopia, hyperopia, astigmatism, presbyopia and/or other optical wave guiding power. For example, the device is a contact lens, sclera lens, or ortho-K lens. In another embodiment, the device is a tissue-engineering scaffold, wound-dressing gel, or an ocular bandage, etc. The device does not need to attach to another ocular medical device (such as an optical lens or a contact lens) to achieve a medical function.

The present invention incorporates the following features into the design of an ocular drug delivery device so that it is capable of delivering a drug at a near constant rate (zero-order kinetics), with a high-precision dosage and extended duration (a week or longer).

(a) The drug is primarily dissolved into a reservoir domain which is composed of components with a solubility parameter similar to the drug in order to achieve a high drug solubility.

Figure 1A:
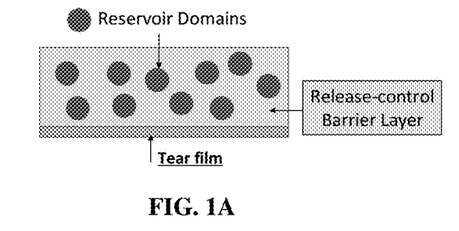
FIGS. 1A and 1B are schematics that detail the position and morphology of drug reservoir domain(s) and barrier layer in a dual-domain contact lens in relevance to the post-lens-tear-film.
Figure 1B:
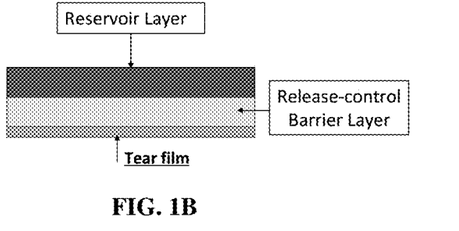

(b) The drug-embedded reservoir domain is either encapsulated as isolated domains within a barrier layer (FIG. 1A), or it is formed as a separate layer in a series contact with a a barrier layer (FIG. 1B). The components of the barrier layer are incompatible to the drug so that the drug has an inherently low solubility within the barrier—leading to a drug's partition predominantly in the reservoir and always near a saturation in the barrier. The in-series arrangement of drug's diffusion path from a reservoir, through a barrier of extremely low drug solubility, and into the post-lens-tear-film assures the drug release rate from reservoirs be completely controlled by the drug's saturation solubility in the barrier.

(c) The drug solubility partition coefficient between the reservoir domain and the barrier layer is at least 5 to 1, preferable 10 to 1, 30 to 1, 50 to 1, or 100 to 1. Due to the solubility difference between the reservoir domain and the barrier layer and an excessive drug population within the reservoir domain, the device can consistently discharge at a near-constant rate with high-precision dosages dictated by the saturation solubility in the barrier layer for a long period of time.

Solubility Saturation in the Barrier Layer

Figure 2:
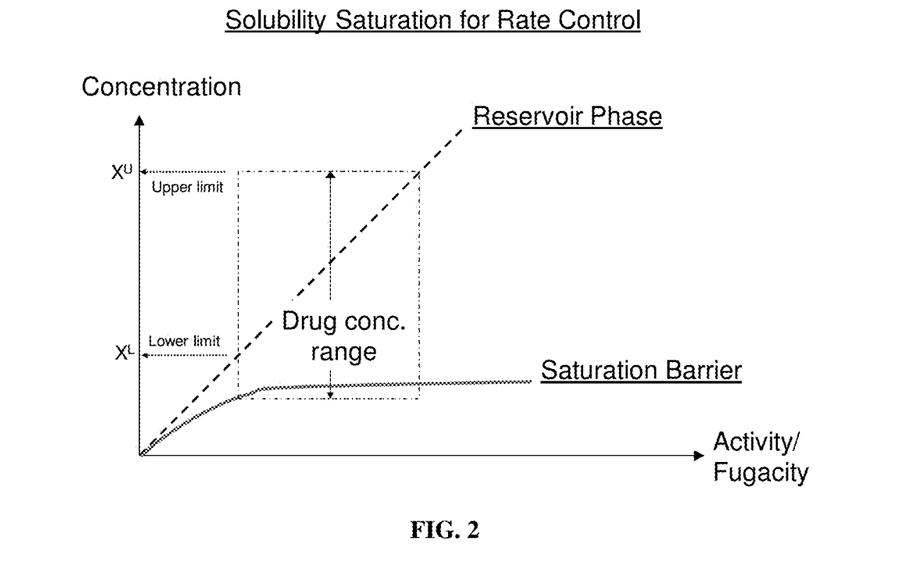
FIG. 2 is a schematic showing how drug partition between the reservoir and barrier layer maintained at the same drug activity (fugacity). The decrease in drug concentration in a long-term delivery, the tapering off of the drug activity at the barrier boundary due to the concentration drop in reservoir domain throughout the delivery period will cause very little concentration change in barrier layer because of the barrier saturation. Drug concentration in the barrier layer is always near a constant despite the drug concentration variations within a range, $X^L$ to $X^U$, which leads to a constant-rate drug release throughout the delivery.

The substantial difference of drug solubility in the reservoir domain and barrier layer is illustrated in FIG. 2. The solubility behavior generally follows the rule of like-dissolve-like. A hydrophobic drug has a higher solubility in a hydrophobic medium but very limited solubility in a hydrophilic environment. For a definition of the hydrophobic and hydrophilic nature of a component, one can use the log P octanol/water as a reference point, where P is a partition coefficient of a solute between octanol and water. A positive log P value means hydrophobic and a negative log P value means hydrophilic. A differential of log P less than 0.5 between two components means they are of a similar (alike) nature, while a differential of log P greater than 1 means the two components are of opposite (dislike) nature.

The ocular device of the present invention is a dual domain device, which contains a reservoir domain with a similar (alike) log P to the drug and a barrier layer with a very different (dislike) log P to the drug so that the drug has a substantially higher (e.g., ten times or more) solubility in reservoir than in barrier. The reservoir domain is referred to as the "drug-like domain" and the barrier layer as the "drug-dislike domain." The large disparity in drug solubility of the two domains has created a drug concentration window within which the change in drug's fugacity/activity (~Exp ($\Delta\mu/kT$), where $\Delta\mu=\mu-\mu^\circ$ is the drug's chemical potential relative to a reference standard state) corresponds to a proportionally substantial concentration change in the reservoir domain but almost constant concentration in the barrier layer due to the saturation effect. When an ocular device is operating within this drug concentration range in the reservoirs, the drug concentration in the barrier layer remains almost constant (saturation effect) throughout the entire delivery period. For each specific drug delivery, the initial highest drug concentration in reservoir, $X^U$, is loaded according to clinically established efficacy and safety levels. The drug delivery is essentially at a constant rate due to the barrier saturation (details elaborated in the next section) until the reservoir concentration drops to a lower bound $X^L$, below which the reservoir concentration is not sufficient to maintain barrier saturation anymore. Beyond this point, the drug delivery rate is no longer be a constant and, in fact, diminishes proportionally following the depletion of the residual reservoir drug level below $X_L$. The lower a drug solubility in a barrier layer, the smaller the $X_L$ of reservoir concentration level. For any specific drug, the ratio $R_x=X^U/X^L$, defined as the drug's reservoir/barrier saturation ratio, is higher with increasing drug solubility difference between reservoir and barrier, while the ratio $1/R_x$, indicates the last delivery portion not achieving the precision of a constant rate.

Delivery Rate Controlled by the Barrier Layer

Figure 3:
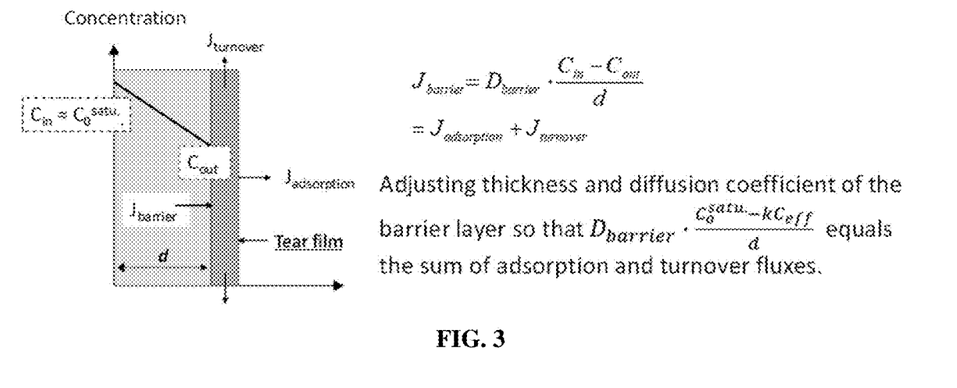
FIG. 3 is a schematic and supporting mathematical equations showing how constant drug delivery rate due to solubility saturation of barrier layer by the drug in the reservoir.

The drug's steady-state permeation rate thorough a barrier layer can be precisely prescribed by the multiplication product of a diffusion constant (a material property of the barrier) to the drug's concentration gradient in the barrier, the latter of which can be expressed as $$\frac{C_{in} - C_{out}}{t},$$

where t is the thickness of a barrier. The barrier must be positioned to block the drug diffusion paths from the reservoir domain to the tear film between the device and the ocular surface (e.g., see FIGS. 1A, 1B, and 2) so that it can throttle the drug release as the device' rate-determining step (i.e., the slowest rate in a series of diffusion paths). In a steady state delivery, the drug permeation rate through the barrier must equal the combined rates of corneal adsorption ($J_{adsorption}$) and tear turnover loss ($J_{turnover}$). Once reaching a steady-state, the permeation rate through the barrier remains nearly at a constant due the saturation effect at the boundary of reservoir domains and the barrier layer (i.e. $C_{in}$ is a constant≈$C_{saturation}$). (FIG. 3)

High-Precision Drug Delivery Rate and Dosage to Optimize Corneal Adsorption

The dual-domain ocular device of the present invention separates the functions of drug storage and rate-determination into the respective reservoir and barrier layers, and thus, can achieve the highest precision in the control of rate and dosage of ocular drug deliveries. Eye drops in ocular treatment are known for low delivery efficacy as less than 5-10% are available to the cornea. Eye drop treatments of glaucoma are almost completely empirical with only limited control over efficacy through dosing frequency and concentration. On the other hand, the nanoengineered ocular device of the present invention delivers drugs at a long-term, steady (near constant) rate and with the highest possible precision. For each specific drug, we can combine in-vitro kinetics studies and animal models to first quantify the most effective dosage (i.e. a steady-state concentration in the tear film between the device and the ocular surface matching an optimized corneal adsorption rate), followed by fine-tuning the material properties of the dual domains (e.g., hydrophobic/hydrophilic ratio, degree of crosslinking, barrier thickness, porosity etc.) to deliver the highest-efficacy concentration throughout the treatment period using the device. This approach substantially increases the drug's bioavailability and reduces potentially harmful systemic absorption (estimated to be at least 90% less than by topical eye drops), among many other delivery inefficiencies.

Dual-Domain Design Maximizes Efficacy of an Ocular Device Drug Delivery

In one embodiment, the present invention utilizes the dual-domain technology and transforms the otherwise generic contact lens drug delivery to a custom-designed, ocular device to deliver a specific drug with optimal precision, efficacy, and duration. The dual-domain lens delivery technology of the present invention can precisely and consistently correlate the steady-state drug delivery rate to the material properties of a composite ocular device in terms of hydrophilic/hydrophobic composition ratio of the device and the diffusion speed in the rate-determining barrier layer. Based on a drug's solubility and partition manners with different solvents and among lens' different domains, efficient drug loading processes can be achieved by soaking the dual-domain ocular device of the present invention in a mixture of solvents. Thus, the dual-domain ocular device, besides offering higher quantitative precision than generic lens delivery, can be fabricated with custom-designed composite composition to make its delivery exactly matching the most preferred corneal adsorption rate (provided by animal model in each specific drug case), while make the device's drug loading process sufficiently precise and batch-consistent for mass productions and clinical tests. The high-precision drug loading as well as delivery from a specially designed dual-domain lens are key factors for the commercialization of ocular delivery device.

The permeation rate of a drug through a substrate barrier is generally determined by the product of the drug's solubility (S) and diffusivity (D) in the substrate; i.e. Permeability=S·D. A drug's solubility in a substrate is normally increased with a higher loading concentration at the substrate boundary (normally expressed in terms of activity which is referenced to a standard state and equals to the concentration multiplied by an activity coefficient) until it levels off to a constant near a saturation solubility. Beyond this saturation point, any further increase of concentration at the substrate boundary will not change the concentration within the substrate and thus, will not affect the drug permeation rate in substrate given that the drug diffusion coefficient is a constant. Covering a drug reservoir externally with a continuous barrier layer that has a low saturation solubility and constant diffusion coefficient (a layer with no swelling and no porosity) can achieve a zero-order release because the drug permeability in the barrier is always a constant at the saturation point.

Figure 4:
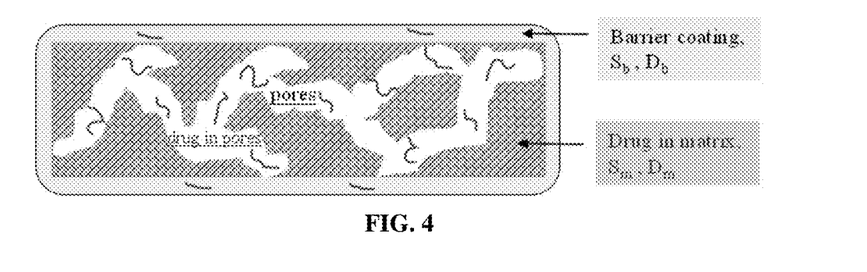
FIG. 4 is a schematic illustrating how a reservoir matrix is surrounded by a barrier layer to regulate its drug release rate by solubility saturation at its boundary with the barrier. The porosity channels are created to facility drug loading by a soaking method.

The practice of a dual-domain design of the present invention is illustrated in FIG. 4. A drug is loaded within a reservoir polymer domain that has a low matrix diffusion coefficient, $D_m$, but is highly compatible to the drug (for example, a hydrophobic drug dissolved within a hydrophobic polymer matrix) leading to a high $S_m$. The polymer matrix contains open-channel pores from which the drug can be quickly equilibrated among nearby reservoir domains. A barrier coating containing no porosity and with very low drug solubility is applied to cover the drug-loaded nanopore polymer matrix of which the drug concentration in the reservoirs, or pores are much higher than the saturation solubility in the barrier, $S_b$, so that the resultant leaching rate is completely regulated by the barrier permeability, $P_b=S_b·D_b$. For example, when the reservoir and barrier components are chosen to have a saturation ratio of 10 (i.e. $R_x=X^U/X^L$~10), an estimated 90% of the drug, $$\frac{X^U - X^L}{X^U} \times 100\%,$$

is released in zero-order rate and the last 10% (100%/$R_x$) in a diminishing rate proportional to the remaining drug level.

In a dual-domain device of the present invention, the solubility difference defined by a drug's reservoir/barrier saturation ratio of $R_x$ is at least 5 to 10, preferably with even higher multiple up to 100. The barrier layer in general requires a diffusive thickness of 0.5-100 μm, preferably 10-100 μm, or 30-100 μm, which inversely proportion to the layer's diffusion constant. The reservoir domain and the barrier layer preferably, but not necessarily, are in direct contact with each other, or connected with pore channels. The connection through open channels facilitates drug adsorption by the reservoir domain in a solution drug loading process.

In one embodiment, the drug is hydrophobic, the reservoir domain is made of one or more hydrophobic components, and the barrier layer is made of one or more hydrophilic components.

In another embodiment, the drug is hydrophilic, the reservoir domain is made of one or more hydrophilic components and the barrier layer is made of one or more hydrophobic components.

The general rule of choosing the reservoir and barrier material components for a specific drug is to make the log P of the reservoir domain very close to log P of the drug. Exactly how close of the log P of reservoir to the drug depends on how much drug solubility is required in the reservoir domain to achieve the desired clinical efficacy. The difference in log P between reservoir and barrier layer is preferred higher than 1, more preferably 2 to 3, or even higher. Using a mixture in a domain is acceptable and sometimes necessary to maintain components compatibility and transparency. There are methods to obtain log P of a composite. In order to also maintain other desired properties of a transparent lens, such as oxygen permeability, water affinity, and flexibility, the hydrophobic and hydrophilic components may be chosen based on ingredients already successfully utilized by hydrogel, silicone-hydrogel, and rigid-gas permeable lenses as listed below in Tables 1A-1C.

For example, the hydrophilic components of the reservoir domain/barrier layer can be selected from any of the hydrophilic components listed in Table 1A, 1B, or 1C, and the hydrophobic components of the reservoir domain/barrier layer can be selected from any of the hydrophobic components listed in Table 1A, 1B, or 1C,

TABLE 1A

Common materials used to make hydrogel soft contact lens

| Hydrophilic component | Hydrophobic component |
|---|---|
| 2-Hydroxyethyl methacrylate ("HEMA") | Methyl methacrylate) ("MMA" |
| N,N-dimethylacrylamide ("DMA") | Isobutyl methacrylate |
| N-vinyl-2-pyrrolidone ("NVP") | Pentyl methacrylate |
| 4,4-Dimethyl-2-vinyl-2-oxazolin-5-one | Cyclohexyl methacrylate |
| Methacrylic acid ("MAA") | Lauryl methacrylate |
| N-(Hydroxymethyl)acrylamide | |
| N-[3-(Dimethylamino)propyl]methacrylamide | |
| Ethylene glycol dimethacrylate | |

TABLE 1B

Common materials used to make silicone-hydrogel soft contact lens

| Hydrophilic component | Hydrophobic component |
|---|---|
| 2-Hydroxyethyl methacrylate | 3-[Tris(trimethylsiloxy)silyl]propyl methacrylate ("TRIS") |
| N,N-dimethylacrylamide | 3-Methacryloxy-2-hydroxypropoxy (propylbis(trimethylsilyloxy) methylsilane ("SIGMA") |
| N-vinyl-2-pyrrolidone | |
| 4,4-Dimethyl-2-vinyl-2-oxazolin-5-one | |
| Methacrylic acid | Fluorosiloxane macromer |
| 2-(Methacryloyloxyethyl)-2-(trimethylammonioethyl) phosphate | Mono-(3-methacryloxy-2-hydroxypropyloxy)propyl terminated, mono-butyl terminated polydimethylsiloxane |
| Ethylene glycol dimethacrylate | |
| Poly(N-vinyl pyrrolidone) ("PVP") | |
| Triethyleneglycol dimethacrylate | Mono-methacryloxypropyl terminated polydimethylsiloxane |

TABLE 1C

Common materials used to make rigid gas permeable ("RGP") contact lens

| Hydrophilic component | Hydrophobic component |
|---|---|
| 2-Hydroxyethyl methacrylate | Methyl methacrylate |
| Methacrylic acid | Trifluoroethy methacrylate |
| Ethylene glycol dimethacrylate | Hexafluoroisopropyl methacrylate |
| Neopentyl glycol dimethacrylate | 3-[Tris(trimethylsiloxy)silyl]propyl methacrylate |
| | Pentacontamethyl-α,ω-bis-(4-methacryloxybutyl) pentacosasiloxane |
| | 1,3-Bis(3-methacryloxypropyl) tetrakis(trimethylsiloxy)disiloxane |
| | Bis hexafluroisopropyl itaconate |
| | Fluoro-siloxanyl styrene |

All present contact lenses are made from acrylic oligomers, or prepolymers by a thermal curing (100° C.-120° C.) process followed by an extensive cycle of washing and sterilization. A drug can be incorporated in a lens either before, or after the lens fabrication process. The pre-fabrication loading of a drug by mixing with lens ingredients is easy, but protecting a drug from thermal degradation, or loss during the washing cycle could be challenging. By examining a drug's solubility and partition coefficient among the relevant solvent(s) and lens components, we can design a post-fabrication drug loading scheme to precisely load the desired drug dosage in a finished lens. One key is to utilize the prefabricated porosity channels (20-40% porosity) to accelerate the loading kinetics. The composition and conditions of the soaking solution can also be manipulated (for example, utilizing temperature, or supersaturation) to promote the drug's faster adsorption into the reservoirs.

In one embodiment, the invention is directed to a drug-eluting contact lens, which provides controlled and sustained release of the therapeutic agent when contacting the eye, by incorporating (1) a hydrophobic drug (for example, bimatoprost, log P~3.2) in reservoirs made of one or more hydrophobic components listed in Table 1B, embedded within a continuous barrier made of one or more hydrophilic components listed in Table 1B, along with chemical additives for curing and crosslinking and 20% inert solvents for porosity creation;

(2) or, a hydrophilic water-soluble drug (for example timolol maleate, log P~1.4) in reservoirs made of one or more hydrophilic components listed in Table 1B and cover the reservoirs with a continuous barrier composed of one or more hydrophilic components listed in Table 1B; along with chemical additives for curing and crosslinking and 20% inert solvents for porosity creation;

such that the reservoir/barrier saturation ratio is ten or higher and the barrier thickness (10-100 microns) adjusted to control the constant release rate to the desired level (for example, 20 µg/day for a week).

In another embodiment, a drug-eluting contact lens can be fabricated by pre-forming, or pre-synthesizing drug-philic reservoir components in domains of block-copolymers, nanoparticles, liposomes, micelles, etc., and in shapes of needles, rods, disks etc., followed by incorporating these reservoir domains within a continuum of drug-philic barrier components cured by free radical polymerization, condensation reaction, gelation, or drying. The drug can be loaded by solution soaking or solvent exchange in making reservoir particles, or solution soaking of the finished devices.

In one embodiment, a drug-eluting contact lens can be fabricated by reacting the drug-philic reservoir components to a form of a condensed state of a polymer, a gel, a block-copolymer, a nanoparticle, a surface-modified nanoparticle, a connected nanodomain, and an interpenetrating network. The drug in the reservoir layer may be entrapped within a porous nanoparticle to prevent unintentional burst release of the drug from the reservoir layer. For example, a hydrophobic drug can be dispersed into the pores of a hydrophilic nanoparticle made of alginate and/or chitosan, and the interpenetrating network of alginate or chitosan can function as a hydrophilic barrier either for slowing down a drug release, or preventing its burst release as an extra safety control measure.

Using several additional options, we address the safety control of the drug delivery device. Because the delivery rate is completely regulated by the low permeation rate within the barrier layer, both the geometry of and the permeation rate within the reservoir layer can be flexibly modified without compromising the delivery kinetics so long as the reservoir layer is in series with a barrier layer and its intrinsic drug permeation within the reservoir does not fall short of the drug permeation rate in the bather. The geometry of the drug "reservoir" zone can be changed from a flat film to other morphologies such as nanoparticles for facilitating drug incorporation, domain inclusion, device fabrication, or the drug delivery function as long as its rate is still regulated by a barrier in series.

Figure 10:
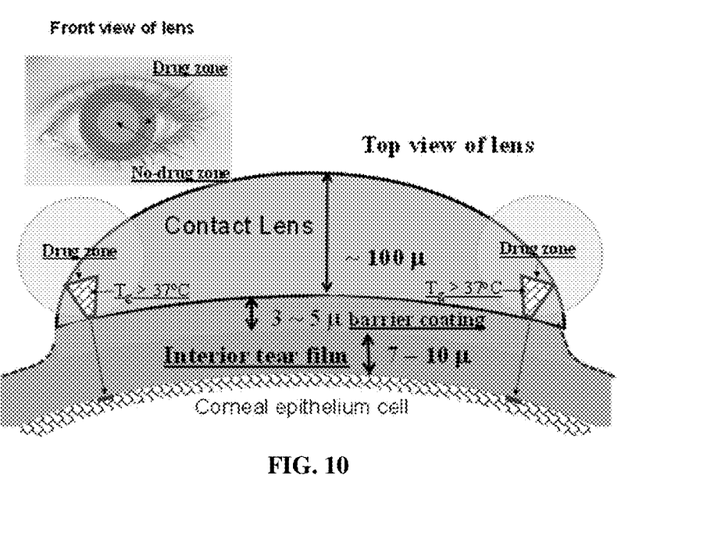
FIG. 10 is a schematic that details the nanoengineered ocular device's position on the eye, and the function of the drug reservoir domain in a wedge configuration.

The drug-eluting ocular device of the present invention optionally includes multiple safety measures to prevent burst failure. Since the majority drug content resides within the reservoir layer, the flexibility of changing morphology and geometry of the reservoir domain can add several safety measures to prevent an accidental storage burst failure. The inventors have developed three additional safety options to eliminate any catastrophic burst failure: (a) hardening the reservoir domain to lower drug diffusion within; (b) entrapping the drug bimatoprost into silica-alginate nanoparticles as an extra barrier; and (c) making the drug reservoir into a wedge-shaped ring with the narrower end facing cornea and functioning as a safety valve. By doing so, the device has another safety valve (narrowing the channel) against leaking into the tear film between the device and the ocular surface. In one embodiment, the reservoir domain is configured into a wedge-shaped geometry with a narrow end facing the ocular surface when placed in the eye and a broad end facing away from the ocular surface (FIG. 10) when placed in the eye, to prevent any accidental over dosing in the tear film between device and eye. In another embodiment, the reservoir domain is configured into a wedge-shaped geometry with the narrow end pointing at a specific area of the ocular surface when placed in the eye to achieve a targeted, location-specific delivery of the drug. Further, the device ensures that even if all other safety measures fail, the leakage will be predominantly through the top surface of the device where tear lacrimation would wash away the majority of overflow, similar to a topical eye drop application. Such a novel structural design also enables the pinpoint precision of a location-specific drug delivery area.

The drug-eluting ocular device of the present invention targets drug delivery to a specific location. We utilize the location of the drug loading zone and the advantage of a short, but direct delivery route to achieve a localized delivery targeted at a specific spot on the surface of the cornea. Such a location-specific delivery is possible only by a direct delivery to ocular surface because the device is centered at a location relatively stationary with respect to the cornea, except occasional lateral movements. A glaucoma, or other, drug can be delivered to a specific location near the edge of the cornea to target prostaglandin receptors in the trabecular meshwork, sclera, and ciliary muscle. Because of the short distance of diffusion (~20 µm) relative to the dimension of the target (a few millimeters), the drug permeation in interior tear film is considered to be unidirectional toward the target (FIG. 3). The targeting of a specific location around the cornea for drug delivery can benefit ocular treatments other than glaucoma as well. For example, the corneoscleral rim of the eye (about 12 mm in diameter of the center) represents a region with unique anatomical properties due to the location of adult corneal epithelial stem cells in the corneal limbus. These stem cells are essential for the healing and regeneration of the corneal epithelium and for preventing scar tissue growth and a targeted delivery of growth factors and/or nutrients will be beneficial to corneal repair or tissue regeneration based treatment.

The following examples further illustrate the present invention. These examples are intended merely to be illustrative of the present invention and are not to be construed as being limiting.

EXAMPLES

The following examples show dual-domain contact lens of the present invention having constant-rate drug delivery. All drug release examples are carried out under sink conditions (using 0.5 ml simulated tear fluid for each lens and replaced by 0.5 ml at each time point) to simulate the tear exchange mechanism in the real case. All examples have shown a quicker release for a few hours followed by a constant-rate release for over many days. The initial rapid drug release is attributed to the leaching of drug loading solution remaining in the pore channels. The rapid release stage can be eliminated by a post-loading solvent exchange process. This loading process and the subsequent release process all utilize the drug solubility equilibrium among all components that not only provides the most precise deliverable dosage, but also can prevent premature drug release in storage by creating a drug solubility saturation in the storage medium for long-term storage.

Example 1

This example provides an example of fabrication of silicone-hydrogel dual-domain contact lens.

The soft contact lenses were prepared by polymerizing 2-hydroxyethyl methacrylate (HEMA 8%) along with highly oxygen permeable silicone monomer SIGMA (30%), N.N-dimethylacrylamide (DMA~30%), n-hexanol (23% to create porosity), free-radical thermal initiator 2,2'-azobis-(2-methylpropionitrile) AIBN, polyvinylpyrrolidone K-90 (5% for wetting) and ethylene glycol dimethacrylate (EGDMA, 1% for crosslinking). The mixture of monomer mixed was injected into a polypropylene contact lens mold. After curing at 120° C. for 2 hours, contact lenses were washed with isopropanol and water mixture (50%, v/v) to remove initiator residue and unreacted monomers. For nanoparticle loaded contact lenses, nanoparticles were added into pre-cured monomer solution subsequent to polymerization.

Example 2

Silicone-hydrogel lens loaded with bimatoprost (a hydrophobic drug, log P~3.2) by soaking lens in hydrophobic solvent hexanol (log P=2.03): For the drug loading process, three silicone hydrogel soft contact lenses were soaked in 0.5 ml bimatoprost hexanol solution with a concentration of 50 mg/ml for two days; another three soft contact lenses were soaked in 0.5 ml bimatoprost hexanol solution with a concentration of 25 mg/ml for two days. Each group of lenses was rinsed in 5 ml water for 30 seconds.

For the in vitro release condition, each lens was placed in 0.5 ml phosphate buffer (pH 7.5, 10 mM), at predetermined time intervals, 0.5 ml release medium was withdrawn and replaced with fresh phosphate buffer to simulate the tear exchange sink condition. The amount bimatoprost released into the phosphate buffer medium was measured using a UV/VIS spectrophotometer at a wavelength of 210 nm. Concentrations and masses of released bimatoprost at each kinetic time point were calculated based on a calibration curve prepared with known bimatoprost concentrations ($R^2 > 0.99$).

Figure 5:
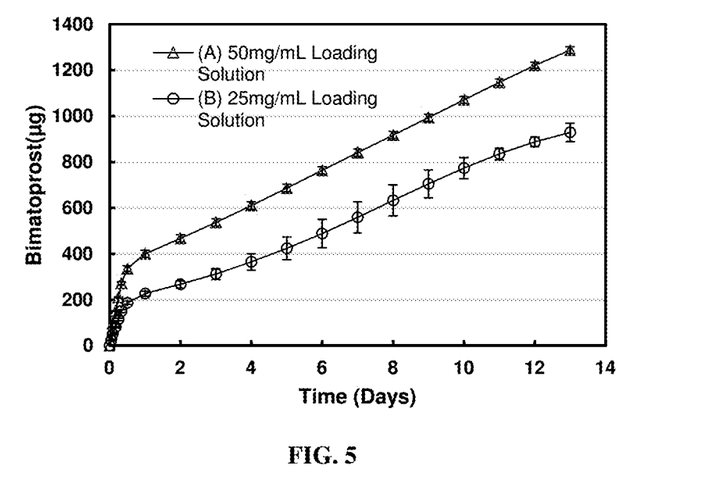
FIG. 5 is a plot showing the cumulative release of bimatoprost from a contact lens under sink conditions following loading the contact lens with bimatoprost hexanol solution.

The cumulative mass release profile of the release of bimatoprost over time from the contact lens is plotted in FIG. 5 and shows a constant rate of sustained release of the drug for 12 days. Hexanol is a hydrophobic solvent, log P~2, it can dissolve a high amount of bimatoprost and thus, carry a high drug dosage into the silicone hydrophobic reservoir domain of the contact lens or ocular device. Hexanol loading at high bimatoprost concentration can achieve constant rate release due to saturation of the hydrophilic barrier domain formed from the polymerization of HEMA and DMA components of the contact lens.

Example 3

Silicone-hydrogel contact lens loaded with bimatoprost by soaking lens in a medium with different hydrophilicity—Water and Water/Isopropanol (IPA) mixture (50% v/v): For the drug loading process, three soft contact lenses were soaked in 1 ml bimatoprost water/isopropanol (50% v/v) solution with a concentration of 0.5 mg/ml for two days; another three soft contact lenses were soaked in 1 ml bimatoprost water solution with bimatoprost concentration of 0.5 mg/ml for two days. Each group of lenses was rinsed in 5 ml water for 30 seconds.

For the in vitro release condition, each lens was placed in 0.5 ml phosphate buffer (pH 7.5, 10 mM), at predetermined time intervals, 0.5 ml release medium was withdrawn and replaced with fresh phosphate buffer to simulate tear exchange sink condition. The amount bimatoprost released into the phosphate buffer medium was measured using a UV/VIS spectrophotometer at a wavelength of 210 nm.

Figure 6:
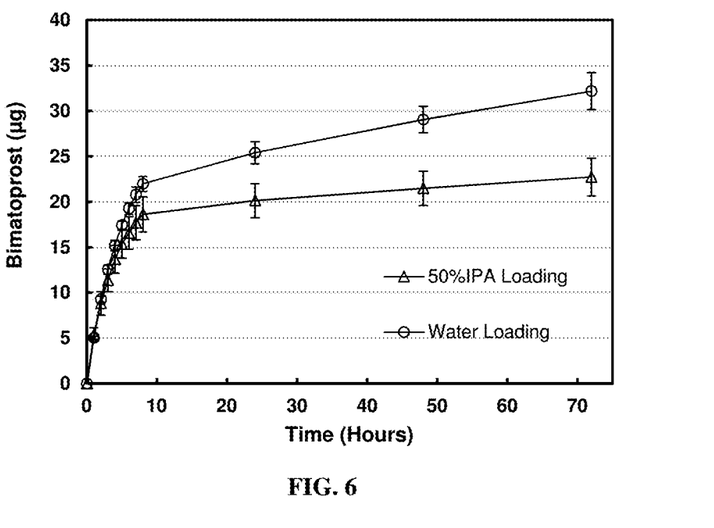
FIG. 6 is a plot showing the cumulative release of bimatoprost from a contact lens under sink conditions following loading the contact lens with bimatoprost dissolved in solutions with different hydrophilicity.

The cumulative mass release profile of the release of bimatoprost from the contact lens is plotted_in FIG. 6. The contact lens in water loading condition showed slightly higher release amount compared to the silicone hydrogel contact lens in isopropanol (50% v/v) loading condition. Isopropanol is less hydrophobic (Log P=0.05) then hexanol, but more hydrophobic than water. The isopropanol and water mixture can dissolve more bimatoprost than pure water. At the same drug loading (0.5 mg/ml) concentration, the drug's activity (fugacity) in water/isopropanol mixture is higher than in water and can load a higher amount of bimatoprost into the hydrophobic reservoir.

Example 4

Silicone-hydrogel lens loaded with cyclosporine A (a hydrophobic drug) by soaking in ethanol solution: For the drug loading process, three soft contact lenses were soaked in 2 ml cyclosporine A ethanol solution with a concentration of 3 mg/ml for two days. Each group of lenses is rinsed in 5 ml water for 30 seconds.

For the in vitro release condition, each two lenses were placed in 0.5 ml phosphate buffer (pH 7.5, 10 mM), at predetermined time intervals, 0.5 ml release medium was withdrawn and replaced with fresh phosphate buffer. The amount cyclosporine A released into the phosphate buffer medium was measured using a UV/VIS spectrophotometer at a wavelength of 205 nm. Concentrations and masses of released cyclosporine A at each kinetic time point were calculated based on a calibration curve prepared with known cyclosporine A concentrations ($R^2 > 0.99$).

Figure 7:
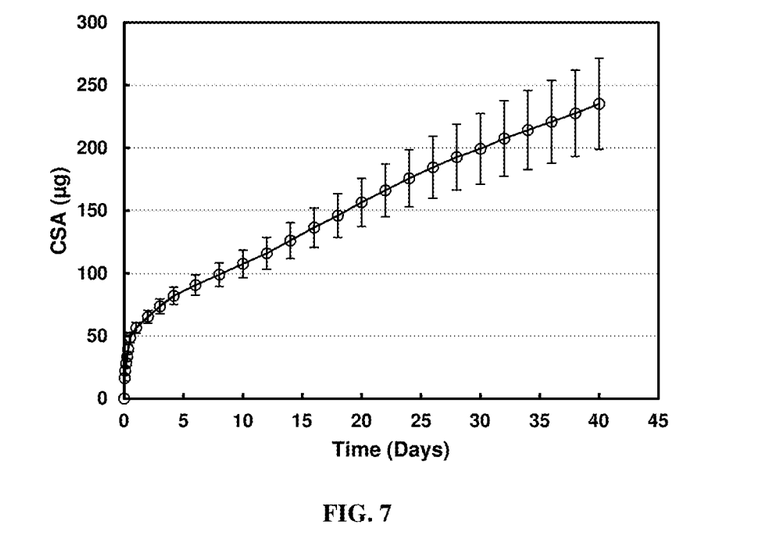
FIG. 7 is a plot showing the cumulative release of the drug cyclosporine A (CSA) from a contact lens under sink conditions after loading using ethanolic solutions of CSA.

The cumulative mass release profile of the release of cyclosporine A is plotted as a function of time in FIG. 7. We used ethanol (Log P=0.05) to improve the solubility in loading solution and obtain a constant rate release up to at least 40 days. Cyclosporine A is a hydrophobic (Log P=4.3) noncharged cyclic peptide that confers a high rigidity to the structure and the drug has very low aqueous solubility of 23 m/mL at 25° C. (Miyake K, J Pharm Sci 1999; 88:39-45). This hydrophobic drug has high affinity for the silicone hydrophobic reservoir domain of the contact lens while the hydrophilic domain formed from the polymerization of HEMA and DMA components is an effective barrier to control the release of the drug.

Example 5

Silica-Poly(methacrylic acid) (PMAA) nanoparticles were prepared using a water-in-oil microemulsion system: Initially, 20 mL n-hexanol was dissolved in 60 mL cyclohexane, followed by addition of 6 mL aqueous PMAA (3% w/w) solution. After 5 minutes, 25 mL Triton™ X-100 non-ionic surfactant was added dropwise until the stirred solution became optically transparent. After 10 minutes of vigorous stirring, 500 µL aqueous ammonia solution (29% w/w) was added dropwise, followed by addition of 1.5 mL tetramethyl orthosilicate. The reaction mixture was stirred for 24 hours at 23° C. before addition of 100 mL acetone to break the stability of the microemulsion. The nanoparticles were recovered by centrifugation (4500 rpm, 10 minutes) and then were washed three times with isopropanol and deionized water to remove the excess surfactant and cosurfactant.

Bimatoprost loaded silica-PMMA nanoparticles: Bimatoprost was first dissolved in ethanol to make a 5 mg/mL solution. Then silica-PMMA nanoparticles were added into 100 µL of this solution. The mixture was incubated at 23° C.

for 5 hours and dried in an oven at 80° C. for 12 hours. The drug loaded silica-PMMA nanoparticles were washed twice with phosphate buffer solution (10 mM, pH 2.5) to remove surface adsorbed bimatoprost.

In vitro release study: Bimatoprost loaded silica-PMAA nanoparticles were suspended in 0.5 mL phosphate buffer (10 mM, pH 2.5) and phosphate buffer (10 mM, pH 7.5) at 23° C. At predetermined time intervals, all release samples were centrifuged (14800 rpm) for 10 minutes, and 0.5 mL supernatant was withdrawn and replaced with 0.5 mL fresh release medium. The amount bimatoprost released into the phosphate buffer medium was measured using a UV/VIS spectrophotometer at a wavelength of 210 nm. Concentrations and masses of released bimatoprost at each kinetic time point in all release media were calculated based on a calibration curve prepared with known bimatoprost concentrations ($R^2>0.99$). After the release study, the silica-PMAA nanoparticles were dissolved in 1 mL NaOH (1 M) to quantify the bimatoprost left inside the nanoparticles. The percentage of cumulative released bimatoprost was then calculated.

Figure 8A:
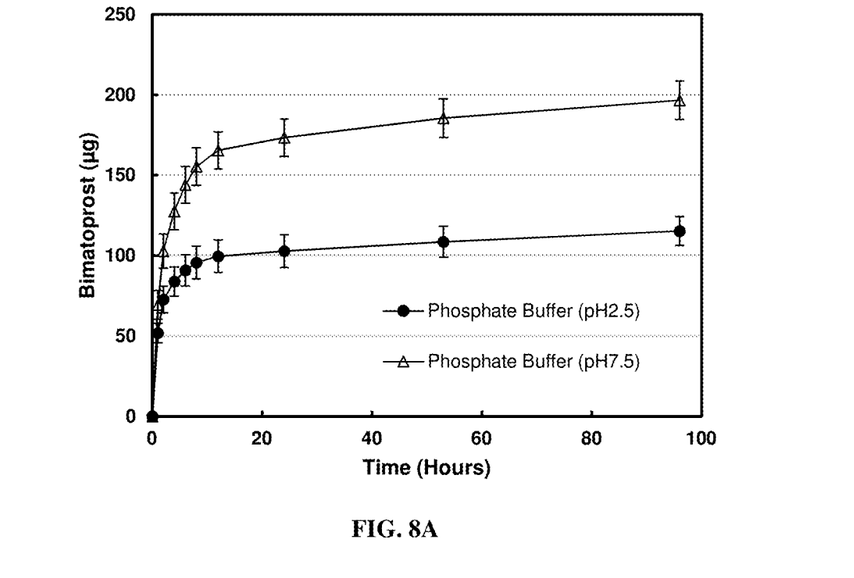
FIG. 8A is a plot showing the cumulative release amount under sink conditions of bimatoprost from silica-PMAA nanoparticles in phosphate buffer with different pH values (pH 2.5 and pH 7.5).
Figure 8B:
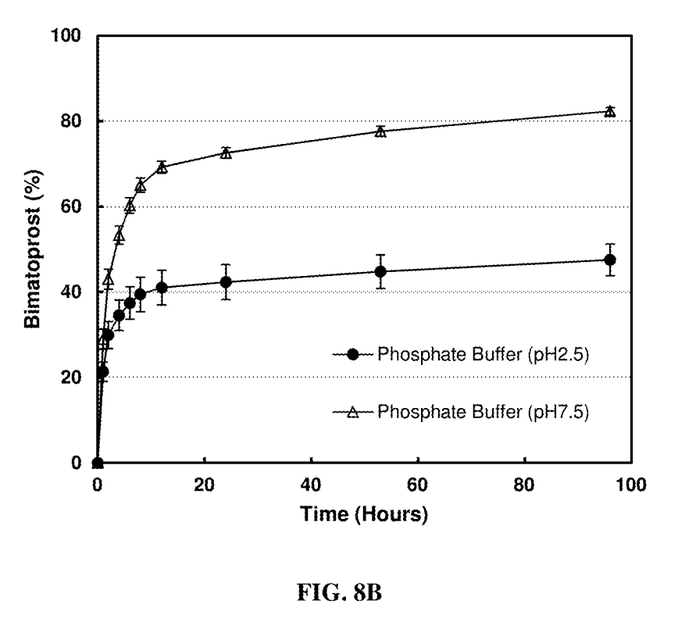
FIG. 8B is a plot showing the cumulative release percentage of bimatoprost, expressed as a percentage of total from bimatoprost loaded silica-PMAA nanoparticles in phosphate buffer with different pH values (pH 2.5 and pH 7.5).

The cumulative mass release profile of the bimatoprost released over time is plotted in FIG. 8A and the corresponding percentage of the bimatoprost released over time is plotted in FIG. 8B. In this example, silica-PMAA nanoparticles showed pH-dependent release ability for loaded bimatoprost, more bimatoprost was released with the higher pH condition. This demonstrates feasibility of constant-rate release in response to changes in environmental condition (pH). Bimatoprost was loaded directly into the nanoparticles and adheres on the pore interfaces after drying. The drug release was directly from the nanoparticles where the simulated tear fluid in the pore channels served as the effective barrier layer because of saturation of the hydrophobic drug.

Example 6

Silica-PMAA nanoparticles were prepared using a water-in-oil microemulsion system: Initially, 20 mL n-hexanol was dissolved in 60 mL cyclohexane, followed by addition of 6 mL aqueous PMAA (3% w/v) solution. After 5 minutes, 25 mL TRITON® X-100 non-ionic surfactant was added dropwise until the stirred solution became optically transparent. After 10 minutes of vigorous stirring, 500 µL aqueous ammonia solution (29% w/w) was added dropwise, followed by addition of 1.5 mL tetramethyl orthosilicate. The reaction mixture was stirred for 24 hours at 23° C. before addition of 100 mL acetone to break the stability of the microemulsion. The nanoparticles were recovered by centrifugation (4500 rpm, 10 minutes) and then were washed three times with isopropanol and deionized water to remove the excess surfactant and cosurfactant.

Cyclosporine A loaded silica-PMAA nanoparticles: Cyclosporine A was first dissolved in ethanol to make a 10 mg/mL solution. Silica-PMAA nanoparticles were added into 100 µL of this solution followed by sonication to obtain homogeneously dispersed nanoparticles. The mixture was incubated at 23° C. for 5 hours and dried in an oven at 80° C. for 12 hours. The drug loaded silica-PMAA nanoparticles were washed twice with phosphate buffer solution (10 mM, pH 2.5) to remove surface adsorbed cyclosporine A.

In vitro release study: Cyclosporine A loaded silica-PMAA nanoparticles were suspended in 1 mL phosphate buffer (10 mM, pH 2.5) and phosphate buffer (10 mM, pH 7.5) at 23° C. At predetermined time intervals, all release samples were centrifuged (14800 rpm) for 10 minutes, and 0.5 mL supernatant was withdrawn and replaced with 0.5 mL fresh release medium. The concentration of cyclosporine A in all release media was measured using a UV-VIS spectrophotometer at a wavelength of 205 nm.

Figure 9:
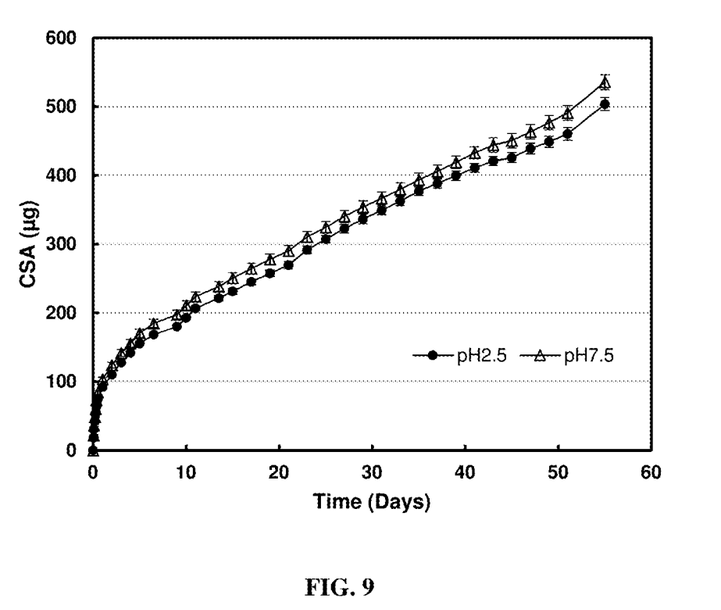
FIG. 9 is a plot showing the cumulative drug release of cyclosporine A loaded silica-PMAA nanoparticles under sink conditions into phosphate buffer with different pH values (pH 2.5 and pH 7.5).

The cumulative mass release profile of the cyclosporine over time is plotted in FIG. 9. Cyclosporine A is even more hydrophobic than bimatoprost and consequently has even lower solubility in simulated tear fluid. The results showed constant rate release for much longer period (for at least 55 days) under both pH conditions due to the effective barrier effect of the simulated tear fluid in the pore channels of the silica-PMAA nanoparticles.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude the specification.

What is claimed is:

1. A transparent ocular device for delivering a drug to the eye of a subject, comprising:
    a drug,
    one or more reservoir domains, and
    a barrier layer configured to control the release of the drug from the reservoir domain to the ocular surface in the eye of the subject,
    wherein the reservoir domain is configured into a wedge-shaped geometry with a narrow end facing the ocular surface
    wherein the drug partitions between the reservoir domain and the barrier layer, and the equilibrium drug solubility in the reservoir domain is at least five folds higher than that in the barrier layer,
    such that when the device is placed directly onto the ocular surface or in contact with a tear film above the ocular surface in the eye, the device provides controlled and sustained release of the drug at a constant rate.

2. The device according to claim 1, wherein the device is not attached to an additional contact lens.

3. The device according to claim 1, wherein the equilibrium drug solubility in the reservoir domain is at least 10 folds higher than that in the barrier layer.

4. The device according to claim 1, wherein the drug is hydrophobic, the reservoir domain is made of one or more hydrophobic components, and the barrier layer is made of one or more hydrophilic components.

5. The device according to claim 4, wherein the one or more hydrophobic components are selected from the group consisting of: methyl methacrylate; isobutyl methacrylate; pentyl methacrylate; cyclohexyl methacrylate; lauryl methacrylate; 3-[tris(trimethylsiloxy)silyl]propyl methacrylate; 3-methacryloxy-2-hydroxypropoxy (propylbis(trimethylsilyloxy) methylsilane; fluorosiloxane macromer; mono-(3-methacryloxy-2-hydroxypropyloxy)propyl terminated, mono-butyl terminated polydimethylsiloxane; monomethacryloxypropyl terminated polydimethylsiloxane; trifluoroethy methacrylate; hexafluoroisopropyl methacrylate; pentacontamethyl-α,ω-bis-(4-methacryloxybutyl) pentacosasiloxane; 1,3-bis(3-methacryloxypropyl) tetrakis (trimethylsiloxy)disiloxane; and bis hexafluroisopropyl itaconate; fluoro-siloxanyl styrene.

6. The device according to claim 4, wherein the one or more hydrophilic components are selected from the group consisting of: 2-hydroxyethyl methacrylate; N,N-dimethylacrylamide; N-vinyl-2-pyrrolidone; 4,4-dimethyl-2-vinyl-2-oxazolin-5-one, methacrylic acid; N-(hydroxymethyl)acrylamide; N-[3-(dimethylamino)propyl]methacrylamide; ethylene glycol dimethacrylate, 2-(methacryloyloxyethyl)-2-(trimethylammonioethyl) phosphate; ethylene glycol dimethacrylate; poly(N-vinyl pyrrolidone), triethyleneglycol dimethacrylate; and neopentyl glycol dimethacrylate.

7. The device according to claim 1, wherein the drug is hydrophilic, the reservoir domain is made of one or more hydrophilic components and the barrier layer is made of one or more hydrophobic components.

8. The device according to claim 7, wherein the one or more hydrophobic components are selected from the group consisting of: methyl methacrylate; isobutyl methacrylate; pentyl methacrylate; cyclohexyl methacrylate; lauryl methacrylate; 3-[tris(trimethylsiloxy)silyl]propyl methacrylate; 3-methacryloxy-2-hydroxypropoxy (propylbis(trimethylsilyloxy) methylsilane; fluorosiloxane macromer; mono-(3-methacryloxy-2-hydroxypropyloxy)propyl terminated, mono-butyl terminated polydimethylsiloxane; monomethacryloxypropyl terminated polydimethylsiloxane; trifluoroethy methacrylate; hexafluoroisopropyl methacrylate; pentacontamethyl-α,ω-bis-(4-methacryloxybutyl) pentacosasiloxane; 1,3-bis(3-methacryloxypropyl) tetrakis (trimethylsiloxy)disiloxane; and bis hexafluroisopropyl itaconate; fluoro-siloxanyl styrene.

9. The device according to claim 7, wherein the one or more hydrophilic components are selected from the group consisting of: 2-hydroxyethyl methacrylate; N,N-dimethylacrylamide; N-vinyl-2-pyrrolidone; 4,4-dimethyl-2-vinyl-2-oxazolin-5-one, methacrylic acid; N-(hydroxymethyl)acrylamide; N-[3-(dimethylamino)propyl]methacrylamide; ethylene glycol dimethacrylate, 2-(methacryloyloxyethyl)-2-(trimethylammonioethyl) phosphate; ethylene glycol dimethacrylate; poly(N-vinyl pyrrolidone), triethyleneglycol dimethacrylate; and neopentyl glycol dimethacrylate.

10. The device according to claim 1, which comprises one reservoir domain in a form of a layer.

11. The device according to claim 1, which comprises multiple reservoir domains embedded within the barrier layer.

12. The device according to claim 1, wherein the reservoir domains are nanocomposites comprising block-copolymers, nanoparticles, liposomes, or micelles.

13. The device according to claim 1, wherein the reservoir domain is hardened to raise the glass transition temperature, or crosslinked to prevent a storage or application burst failure.

14. The device according to claim 1, wherein the reservoir domain comprises hardened or crosslinked nanoparticles to prevent a storage or application burst failure.

15. The device according to claim 1, wherein the reservoir domain is configured into a wedge-shaped geometry with a narrow end facing the ocular surface when placed in the eye and a broad end facing away from the ocular surface when placed in the eye, to prevent any accidental over dosing in the tear film between device and eye.

16. The device according to claim 1, wherein the reservoir domain is configured into a wedge-shaped geometry with the narrow end pointing at a specific area of the ocular surface when placed in the eye to achieve a targeted, location-specific delivery of the drug.

17. The device according to claim 1, which is a contact lens, a scleral lens, an orthokeratology lens, or a corneal bandage.

* * * * *